United States Patent [19]

Kruger et al.

[11] Patent Number: 5,221,204
[45] Date of Patent: Jun. 22, 1993

[54] DENTAL IMPLANT PRODUCT AND METHOD OF MAKING

[76] Inventors: Bernard M. Kruger, 5 Natalie Dr., West Caldwell, N.J. 07006; Lawrence A. Weinberg, 215-35 23rd Ave., Bayside, N.Y. 11360

[21] Appl. No.: 763,534

[22] Filed: Sep. 23, 1991

[51] Int. Cl.⁵ .................... A61C 8/00; A61C 13/12; A61C 13/225
[52] U.S. Cl. .................... 433/173; 433/172; 433/174
[58] Field of Search ............ 433/172, 173, 174, 215, 433/176

[56] References Cited

U.S. PATENT DOCUMENTS

| | | | |
|---|---|---|---|
| 3,474,537 | 10/1969 | Christensen | 433/174 |
| 4,516,937 | 5/1985 | Bosker | 433/173 |
| 4,522,592 | 6/1985 | Ashkinazy | 433/173 |
| 4,784,608 | 11/1988 | Mays | 433/172 |
| 4,799,886 | 1/1989 | Wimmer | 433/176 |
| 5,052,928 | 10/1991 | Anderson | 433/172 |

Primary Examiner—Cary E. O'Connor
Assistant Examiner—Cindy A. Cherichetti
Attorney, Agent, or Firm—Ralph T. Lilore

[57] ABSTRACT

A dental implant is described which has greater stability in the jawbone and greatly reduces the potential for infection. The implant is made from an anatomically precise reproduction of the affected site of the jawbone, which reproduction is produced from computer generated data defining the affected site. The reproduction is used as the base for a cutting jig to fit on an exposed mandible or maxilla and the jig is used to route out a channel which will accommodate the implant. The technique allows the identification and location of sinuses, nerves, and compact bone and thus favors the placement of anchoring means in appropriate areas.

8 Claims, 6 Drawing Sheets

DENTAL IMPLANT PRODUCT AND METHOD OF MAKING

BACKGROUND OF THE INVENTION

This invention relates generally to surgically implantable prostheses and more particularly to endosteal implants. More particularly and definitively it relates to osseointegratable dental implants and prosthetic devices associated therewith It further relates to a process for preparing the implants and to a process for preparing the mandible or maxilla for reception of the implant and the prosthesis.

Dental implants are used when the patient, for various reasons, requires a prosthetic device to hold one or more artificial teeth in place. For example, the teeth surrounding the portion requiring the prosthesis may be too weak or far apart to provide adequate strength or bridging. The system available in the art largely involves the use of single, free-standing implants placed directly into the bone in the area as near to where the new tooth is needed as possible.

There are a variety of systems currently used and they are all based on the common feature of using a cylindrical shaped or screw-type implant tapped into the bone below the periosteum in either the maxilla or mandible. This cylinder or screw, which serves as the implant device, provides the basis for the support for the subsequently introduced artificial tooth or prosthesis via associated intermediate parts. For example, there are various pieces leading from the implant designed to be anchored into the implant and to lead ultimately out of the gum tissue. These are generally known as abutments. There are, for example, abutment cylinders held by abutment screws, one piece abutment/screw combinations, and other parts of varying designs that lead from the implant out of the bone through the gum and into the mouth. The generic term Θabutment" will be in this specification to refer to the attachment assemblies to the implant that lead therefrom out of the gum and support the prosthesis. This abutment serves as a post and is adapted to receive the prosthesis which provides a support site for the artificial tooth. The implant over time becomes osseointegrated. That is, through natural body occurrences via osteogenesis, it actually integrates with the bone structure into which it is imbedded with concurrent formation of new bone, thus giving a very strong integrated connection to the bone.

Unfortunately, while these materials and implant systems have been successful in many cases, they have, for a variety of reasons, not reached the generally widespread use expected of them. One of these reasons is that the line of connection between the implant in the bone through to the artificial tooth is actually a straight line and is therefore subject to the potential for infection, fibrous encapsulation, and loosening. Since there is a direct connection from the prosthesis to the implant, bacterial infections can occur at that spot and proceed along the implant, and impede, disrupt, and reverse the osseointegration process. What results is a loosening of the implant in the bone structure and an ultimate failure of the system.

Another limitation presented by the current implant systems is that the single implant is not supported by other implants within the bone. Rather, mutual support gained by the joining of more than one implant, is obtained outside the bone via the prosthesis. The splinting effect of joining more than one implant by a prosthesis intraorally, is subject to fit inaccuracies which cause overloading of some implants and the underloading of others. There is no current method for implant prosthetics available for supporting more than one implant endosteally, that is, within the bone itself, presumably for the reason that it is very difficult to prepare an implant which can support a plurality of teeth, and yet at the same time be permanently and reliably affixed to or in the bone structure. Very often the anchoring of the implant is confined mainly to areas wherein the medullary or soft, spongy bone predominates, or sinus cavities and other structures prevent the necessary length required for strength. In the posterior residual alveda ridges there is little opportunity for attaching the implant to the compact bone structure and hence a precarious implant is obtained. Often, the location of the bone causes excessive angulation of the implant, leading to biomechanical overloading and failure.

Another disadvantage in the current system is that because of the direct line between the implant, abutment, and prosthesis, all of the force is directed onto a very small part of the bone.

The barriers preventing production of an implantable device capable of supporting many teeth have been many and severe. Until the present invention, there was no way to address bone with poor bone density, reduced height, or angulation, or spanning spaces larger than one tooth space. Indeed, prior to the invention, there has been no way to prepare an implant which rests within and is securely attached (integrated within) the compact bone, or to implant a device within the bone that can support more than one abutment which is splinted together within the bone and not dependent on the exact fit of an intraoral connection device for mutual support.

SUMMARY OF THE INVENTION

Figure 1:
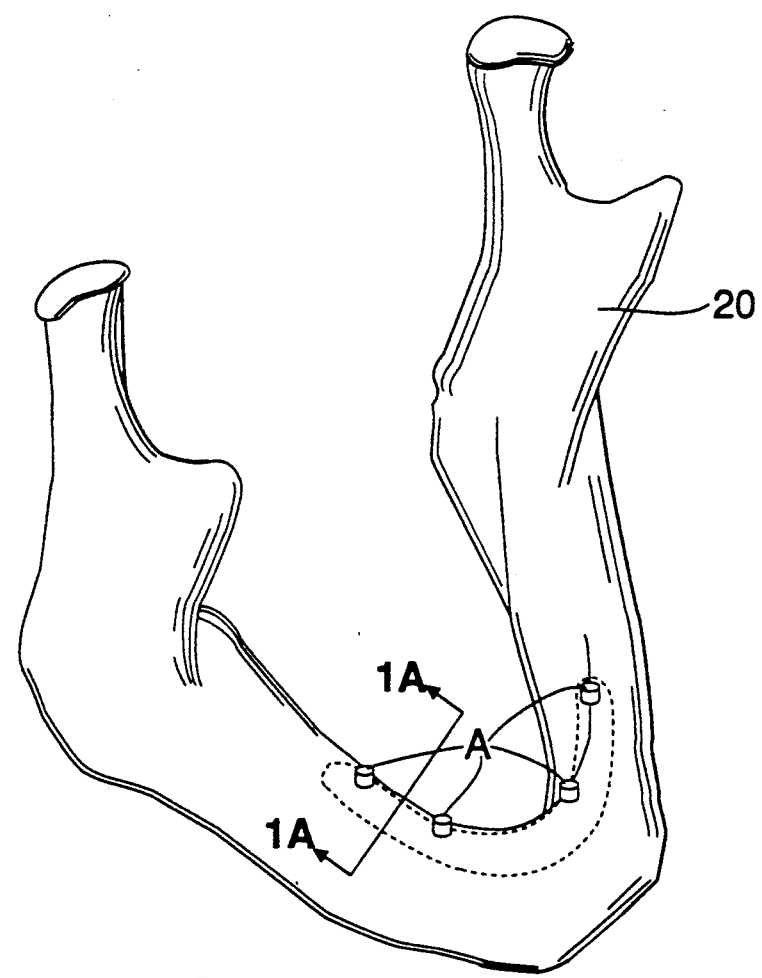
FIG. 1 is a view of a lower jawbone with the fixture of the invention shown implanted into the bone.
Figure 1A:
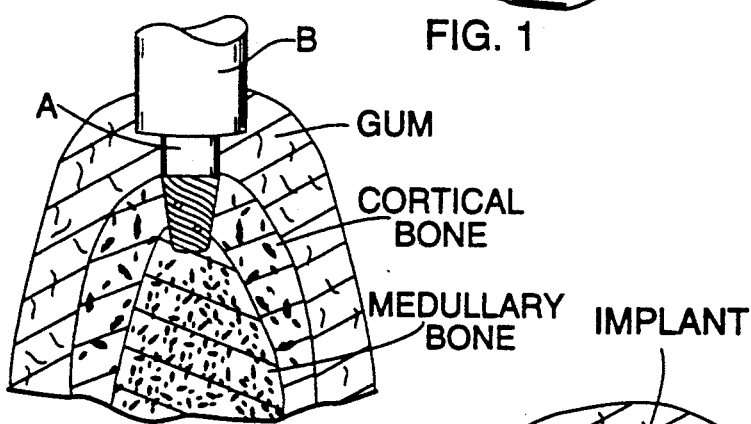
FIG. 1A is a cross sectional view of the implant in the bone with a riser and abutment.
Figure 1B:
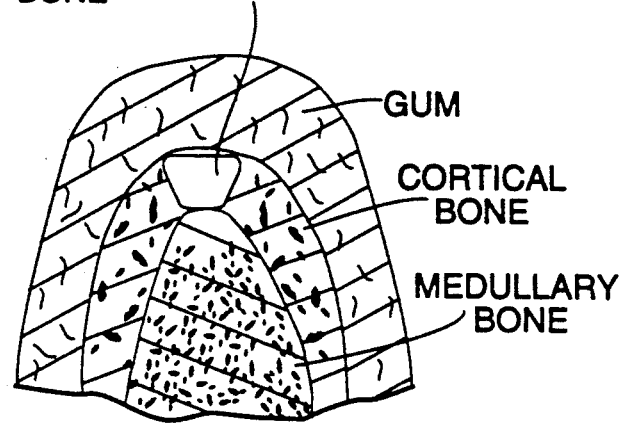
FIG. 1B is a cross sectional view of the implant in the bone without a riser and abutment.

In general, and using the mandible as an example, the process of the invention for producing the product of the invention includes the following:

1. Precise, preferably non-invasive, measurements are taken of the site of interest. It is well within the skill of the art to take these measurements using techniques that are well known and described in the literature. For example, using the non-invasive CT-tomographic scanning technique, magnetic resonance imaging or ultrasound, the precise measurements can be made and three dimensional models of the selected area of the mandible (or maxilla) made directly. U.S. Pat. No. 4,436,684 and its Re-examined Issue B1 4,436,684, describe measuring and contouring techniques whereby three dimensional models corresponding to the entire jawbone, if desired, may be prepared using the computer generated data.

2. From the information generated in Step 1 above, there is produced a model of the affected site. In practice, this might be a small section of the mandible, one tooth for example, or it may be a large portion of the mandible where several or many teeth are missing. This section is reproduced in its entirety preferably in moldable plastic using the generated data and contouring equipment operated in response to the data.

3. From the model produced according to the above steps, a jig is made and adapted so that the bottom of the jig fits onto the top of the mandible, for example. A track running through the jig permits the placement of a drill or routing instrument for routing out a channel in the mandible. The jig is adapted in such a way that the channel to be produced therefrom is sufficient to accommodate the subsequently produced implant, as will be described later, which will provide the basis of the support for the prosthesis. The same techniques used to produce the plastic model of the mandible can be used to produce the jig. The interface between the mandible and the jig should be a tight fitting interface to permit accurate locating of the channel in the mandible and provide adequate tracking for the cutting device to be placed in the jig.

The jig provides the guide for the cutting device to be fit over the bone. In practice, the dentist having the jig and the plastic model available, would expose the mandible surgically and retract the gum from the affected site. The jig would then be placed over the mandible and the channel drilled using appropriate tools. The peaks and valleys of the channel will then correspond to the topography of the jig-bone interface.

4. At some time, preferably prior to the above, though not necessarily, the dentist would have prepared the implant of the present invention, usually of titanium, using normal casting or machining techniques in accordance with personal preferences and expediences. He would have also located within the implantable fixture at the proper angles, a number of holes to accommodate support screws which can be drilled directly into the compact bone. This is done in consideration of the location of the various nerves and sinuses that would be encountered in and near the selected area. These locations are in turn identified by the CT-tomographic scan data and, if desired, located on the plastic model produced therefrom. As mentioned previously, the present invention allows the introduction of support means directly into the tough, strong, compact bone as opposed to the insufficiently supportive medullary bone utilized by the prior art systems. The support screw holes can be aligned in such a way that they are offset from the risers and abutments which come through the gum, thus avoiding the straight line problem discussed previously.

Depending upon the size of the implant, these screw support holes can be aligned in such a way that they will not be aligned directly in line with the riser (or abutment) of the artificial tooth or prosthesis that ultimately comes through the surface of the gum. In that way, a line of infection and/or soft tissue invasion is eliminated, thus avoiding a potentially serious structural weak point encountered by the prior art devices.

5. At the appropriate time, the implant is inserted into the channel which has been drilled out by the dentist using the drill jig described in 3 above. The implant has been manufactured of titanium using techniques well known in the art in such a way as to provide in the implant, certain risers which will serve as the anchoring spots to hold the prosthesis on the implant. For example, assuming that a full mouth dental implant is required, as shown in FIG. 1, the horseshoe shaped implant could be affixed with usually two risers A on each side of the center line, in the canine and molar areas. Prostheses which comprise the appropriate tooth structures and which span and are connected to the risers can be constructed and affixed with the proper abutment B and screw arrangements so as to locate the prostheses into the risers and to support them in the implant.

There may be a wide array of fixtures and ancillary pieces of equipment such as screws, connectors, and the like which will serve to support the prosthesis above the implant.

In accordance with normal dental practice in implantology, as currently performed, a six-month healing period is required after the implantation of the implant into the bone so that osseointegration occurs prior to placement of the artificial tooth prosthesis into the implant. This requires that any risers in the implant be covered by gum tissue and secured in such a way that a) they are easily relocatable six months after implantation, and b) are not covered over with bone structure or other tissue to prevent affixing of the prosthesis. In this regard then it is the normal practice to include plugs (or cover screws) to be inserted into the risers that are permitted to rest under the healing gum during the recuperative period.

In practice, the present invention gives the dentist a wide degree of latitude and flexibility because the initial step of cutting the channel into the bone structure can be accomplished in such a way that the irregularities of any bony ridge that might be encountered, especially in the case of mandibles, is easily removed and/or levelled.

The information necessary to allow the production of the models required for practicing the invention is within the skill of the art as previously noted and is easily obtainable using CT-Tomographic scans, MRI scans, ultrasound scans, or the like. CT-Tomographic scans are preferred. These particular collections of data also identify the location of the sinuses or any particular major nerve system in the area that must be avoided and the dentist working together with the scan data and the model generated therefrom can determine where to place the screws that are necessary to anchor the implant into the compact bony structure.

DETAILED DESCRIPTION OF THE INVENTION

Figure 2:
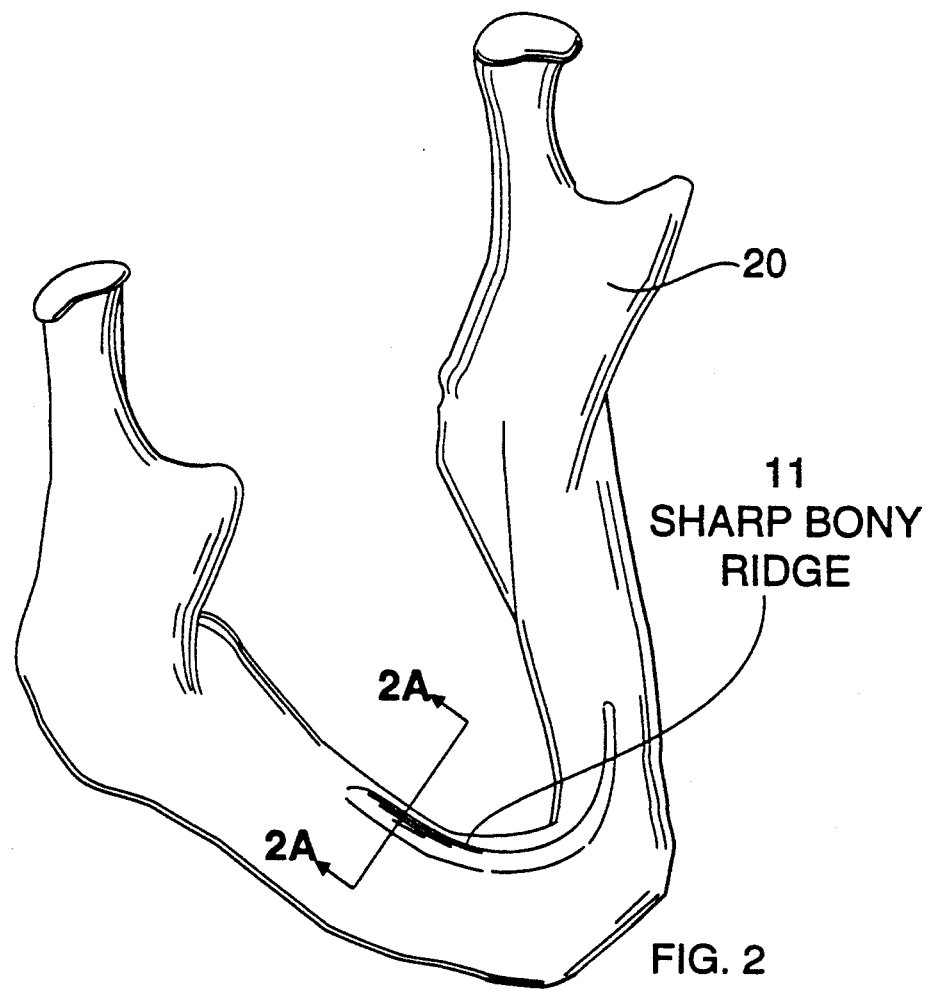
FIG. 2 is a representation of a model obtained form the generation of computer data on a CT-tomographic scan of the mandible.
Figure 2A:
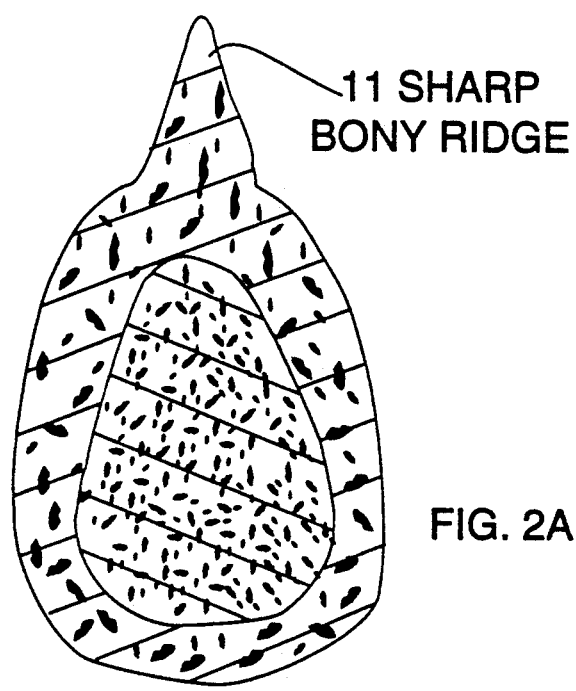
FIG. 2A is a cross section 2A—2A of FIG. 2.

The invention will now be explained with reference to the figures. FIG. 1 has been described hereinabove. FIG. 2 is a representation of the model obtained from the generation of the computer data on a CT-tomographic scan of a mandible. The preparation of this model is within the skill of the art and reflects the art as it is practiced at this time. Specifically, one may obtain from Cemax Corporation, 46750 Fremont Boulevard, Suite 207, Fremont, Calif., 94538, a model of this type by simply having a Catscan performed using the protocol provided by the Company. FIG. 2 shows a full mandible generated according to computer data described above with a cross section taken along lines A—A.

Figure 3:
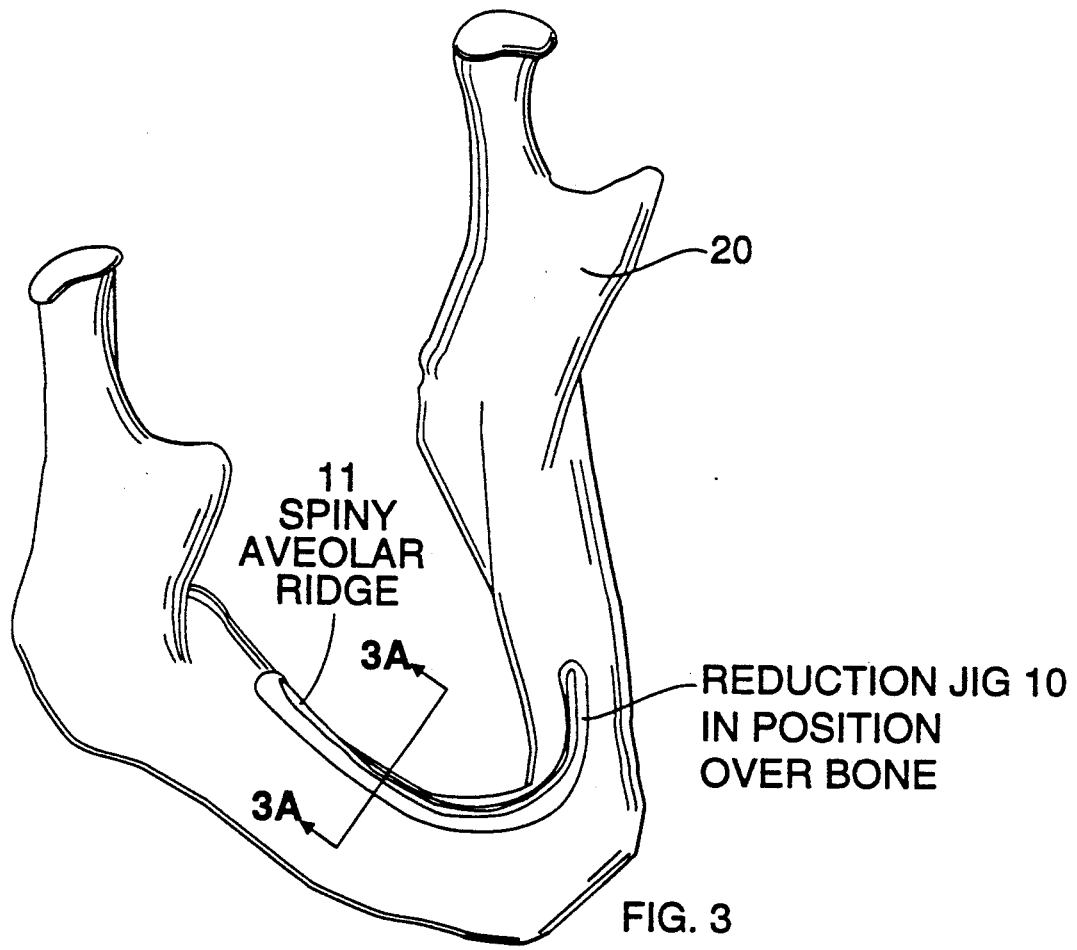
FIG. 3 shows a reduction jig prepared in consideration of the anatomy of the mandible.
Figure 3A:
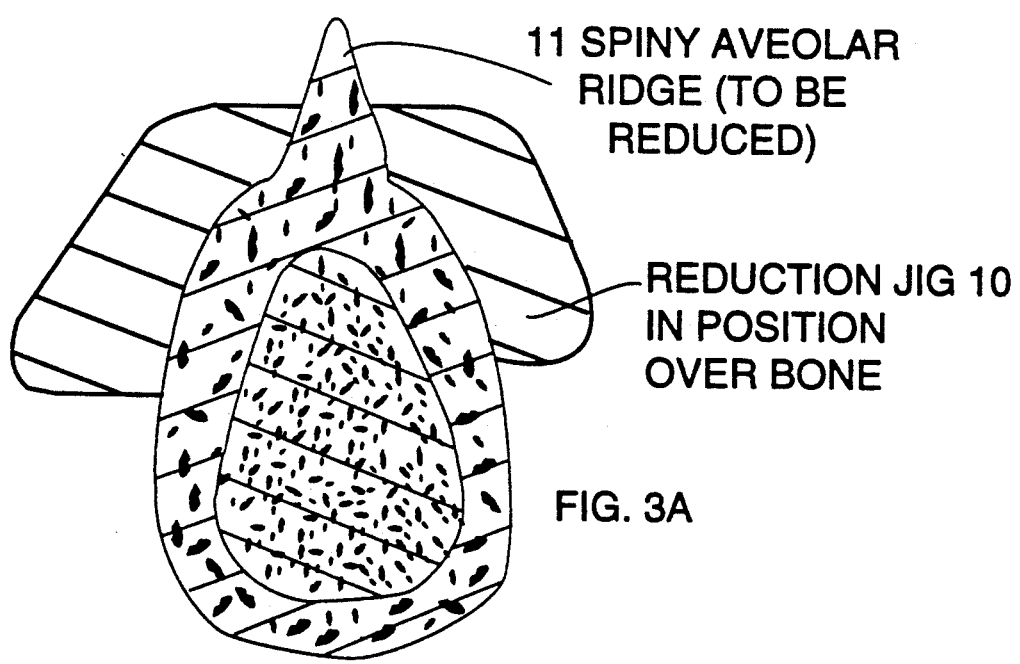
FIG. 3A is a cross section 3A—3A of FIG. 3.

FIG. 3 shows a reduction jig 10 that is prepared in consideration of the anatomy of the mandible 20 with a cross section A—A showing the jig on the mandible. As part of the process for preparing the reduction jig, the dentist evaluates the mandible for irregularities and makes a judgement as to whether such irregularities should be removed and where the implant is best placed. The reduction jig is then made around the mold of the mandible in a size and in proportions that are relevant with regard to the effective removal of spiny ridges and other anatomical structures that might interfere with the size and location of the channel to be drilled into the mandible to accommodate the implant. This particular jig is a preferred, but an optional feature, and is generally used when the removal of any protuberance or spiny ridges on the mandible is desired. In practice, the dentist surgically exposes the site of interest on the jawbone. The reduction jig, prepared in consideration of the irregularities to be removed, is then affixed to the site and a router or drill drawn over the irregularities to level the same. In the case of spiny ridges 11 or the like, the procedure serves to remove the same and results in a flat, level, exposed ridge which can accommodate a channeling or routing instrument subsequently.

Figure 4A:
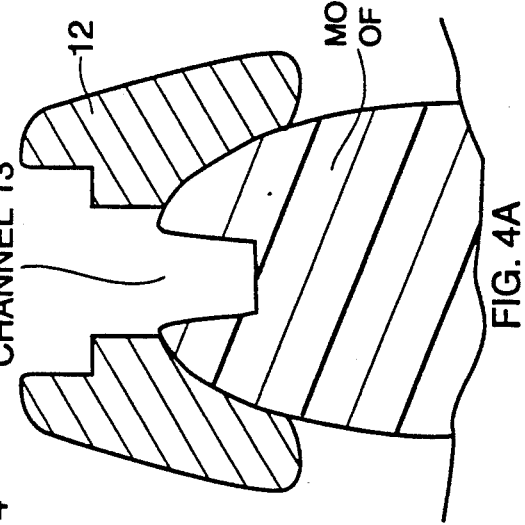
FIG. 4A is a cross section 4A—4A of FIG 4.
Figure 4:
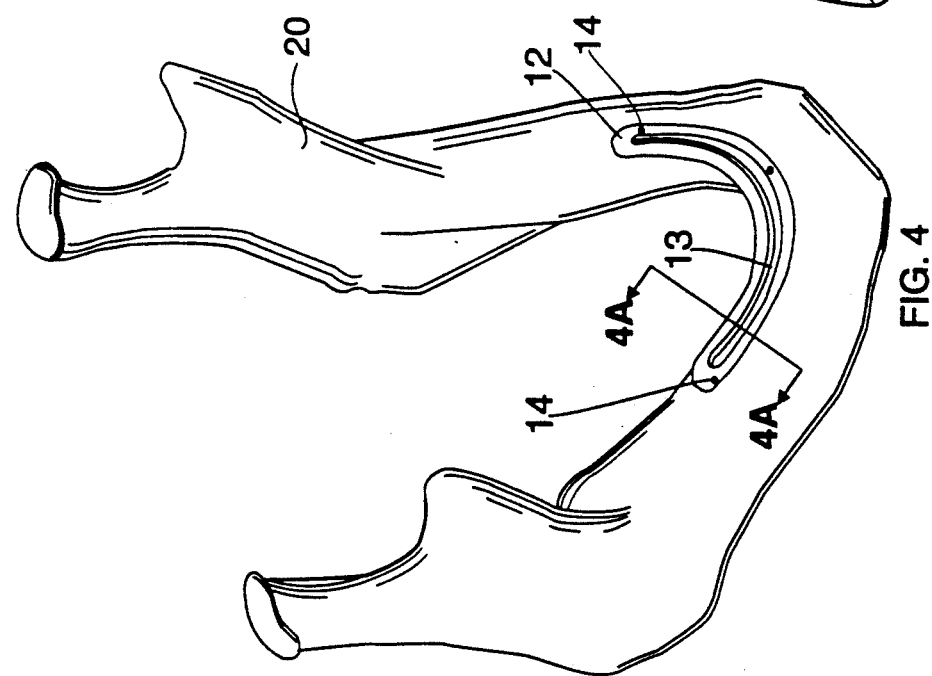
FIG. 4 shows a separate drill jig prepared by molding over the Catscan model shown in FIG. 2.

FIG. 4 shows a separate drill jig 12 prepared by molding over the Catscan model shown in FIG. 2. This jig is most important because it serves to provide the guide which allows the routing of the channel in the mandible to accommodate the implant. The channel in the jig has been prepared in consideration of the size and shape of the desired implant which, of course, in turn, depends in a large measure on the anatomy of the patient and the personal preferences of the dentist and availability of auxiliary materials. In practice, the jig is affixed with screws 14 to the mandible, itself laid bare by the dentist in his preparative work. A drill or routing instrument corresponding to the channel in the drill jig is then run through the jig to drill out the channel necessary to accommodate the implant fixture.

Figure 5:
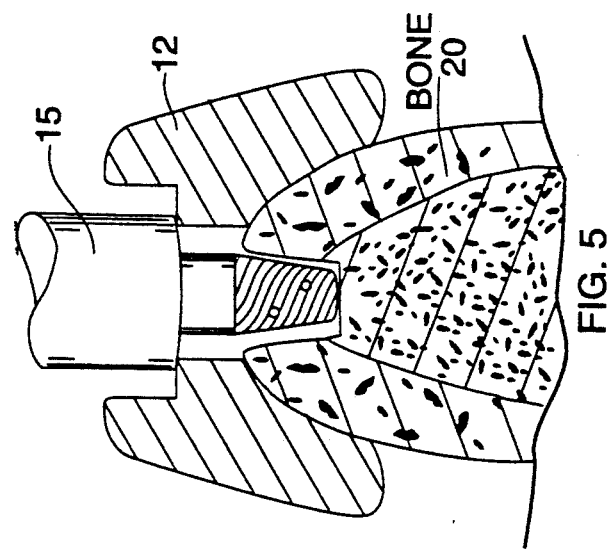
FIG. 5 shows the appearance and cross section of the drill jig located on bone (mandible) with the drill bit enclosed therein in the channelling operation.

FIG. 5 shows the appearance and cross section of the drill jig 12 located on bone 20 (mandible) with the drill bit 15 enclosed therein in the channelling operation.

Figure 6:
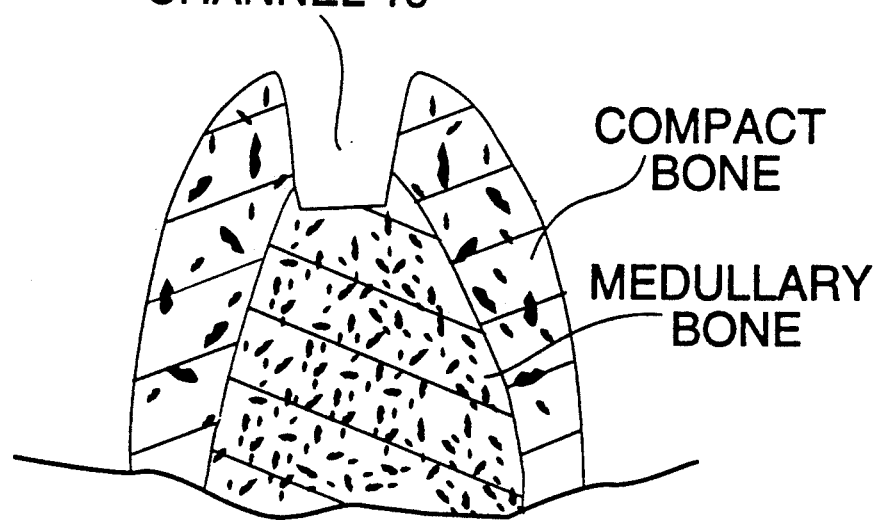
FIG. 6 shows the bone in cross-section after preparation of the implant channel.

FIG. 6 shows the bone in cross-section after preparation of the channel 16.

Figure 7A:
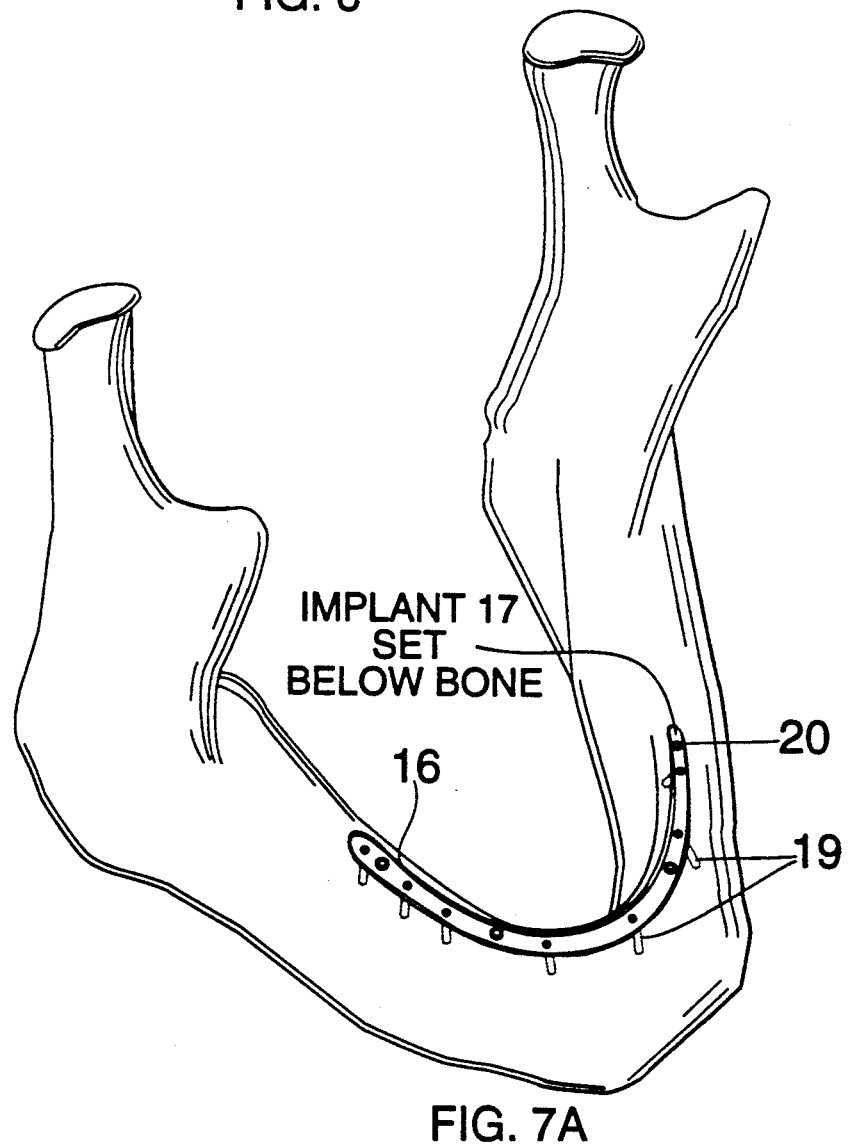
FIG. 7A shows a titanium implant molded or machined to fit into a channel drilled into the mandible.
Figure 7B:
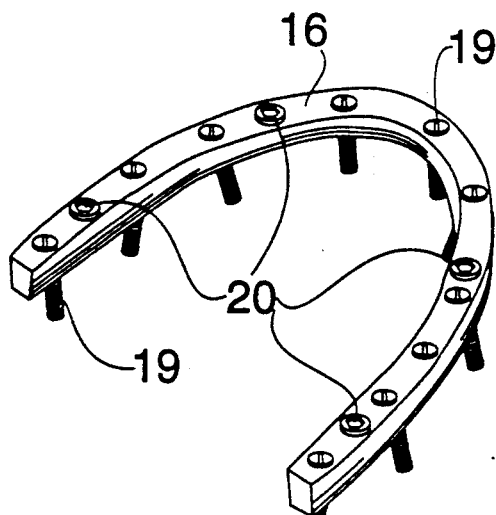
FIG. 7B shows the implant 16 outside of the bone.
Figure 7C:
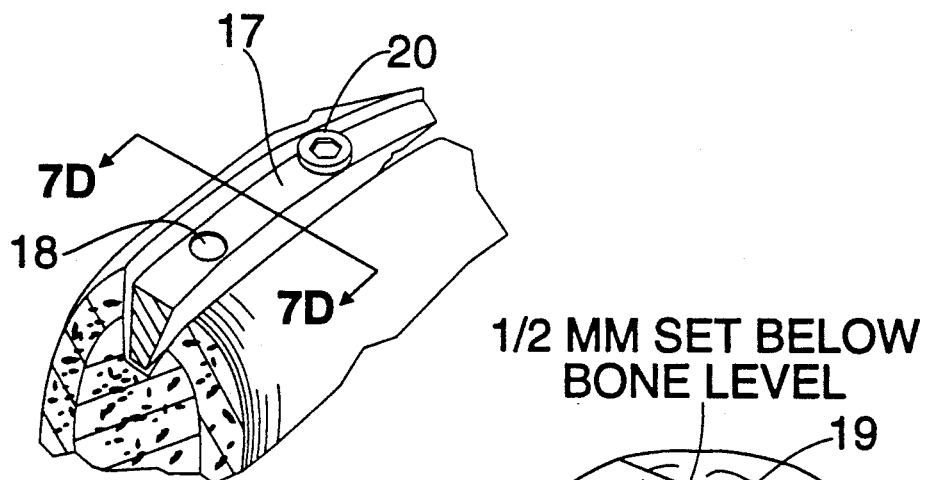
FIG. 7C shows a section of the implant in perspective and FIG. 7D shows the area in cross section.
Figure 7D:
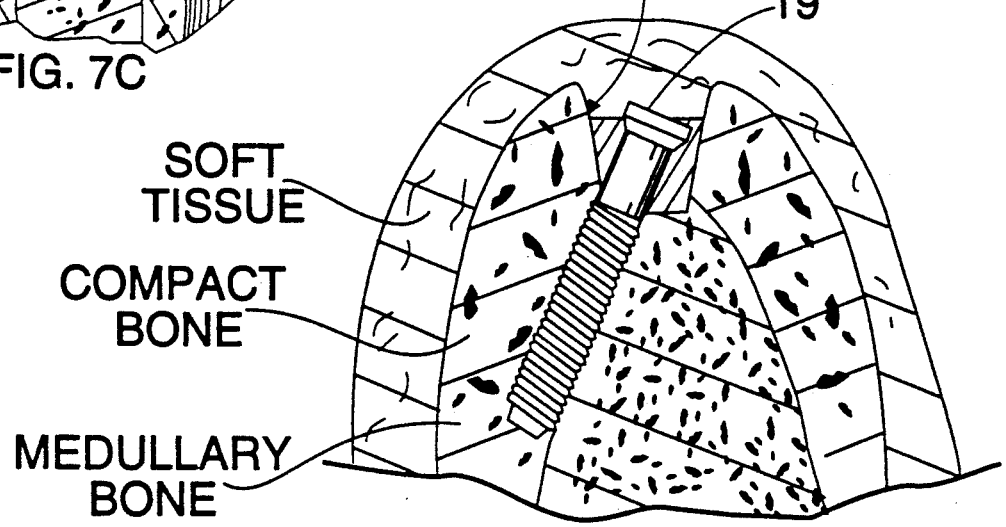

FIG. 7A shows a titanium implant 17 molded or machined to fit into the channel 16 drilled into the mandible. FIG. 7B shows the implant 16 outside of the bone. FIG. 7C shows a section of the implant 16 in perspective and FIG. 7D shows the area in cross section. Screw holes 18 are provided at appropriately placed locations to accommodate screws 19 to be used to anchor the implant into the compact bone. Accordingly, the angles of the screw holes are chosen in consideration of the CT-tomographic scan data so that only compact bone, wherever possible, will be encountered by the screws thereby resulting in the avoidance of medullary bone as an anchoring medium. It will be appreciated by those skilled in the art that the selection of the drill holes will result in a very stable implant fixation in locations that are remote from and not in line with the risers 20 and abutment areas so that a direct line of infection from the prosthesis (not shown) attachable via the risers 20 to the underlying structure is avoided. The number of screws employed can be varied, but it is generally considered that four to six screws per quadrant are adequate. Lateral support is very secure and pressure per screw is minimized because it is evenly distributed over the body of the implant.

With respect to materials of construction, titanium is a biocompatible product and now used very successfully as an implant material for humans and is approved by the FDA. In practice, it has been found that the dental implant is suitably prepared in a casting operation using molten titanium or by machining using appropriate tooling. This aspect is well within the skill of the art.

The implant fixture is provided with a variety of auxiliary pieces to facilitate the reception and anchoring of the prosthesis onto the implant. Such pieces as cover screws for the risers, abutment screws to go directly into the risers, posts, caps, and connectors emanating therefrom are illustrative. The design and manufacture of the prosthesis itself is well within the skill of the art.

The present invention thus makes possible the provision of an implantable framework which does not rely for support upon a direct line from the tooth through the implant and into the bone structure, but rather has a discontinuous line of support and connection to the bone. It also permits the custom preparation of an implant and therefore provides implants which fit directly and precisely into the structure of the given patient as opposed to the systems of the prior art which are manufactured in mass quantities and are utilized in a given patient independently of the needs and specific requirements of the patient's anatomy. Moreover, the invention provides a system whereby a much larger area of osseointegrated implant-bone interface is provided for the implant framework. The splinting action of framework and attachment screws is entirely within osseoinegrated bone, and does not depend on the precise fit of an intraoral prosthesis to provide mutual support. Furthermore, the invention provides a mechanism to bridge areas where very poor quality of bone or shallow bone prevents the utilization of current state of the art individual implants. Thus, anchorage for the implanted support system can be spread out to available bone sites heretofore not usable with the standard individual design.

What is claimed is:

1. A continuous dental fixture for complete implantation into a channel or groove of the jawbone, and osseointegratable therein, means on said fixture for receiving a plurality of screws, the location and direction of said receiving means having determined by reference to anatomical data obtained on the jawbone, which data include the presence and location of compact cortical bone and sensitive vital anatomical structures to be avoided, whereby when screws are inserted into said screw receiving means they are directed to maximize implantation into cortical bone to thereby anchor said fixture into said jawbone and to minimize the engagement with said sensitive anatomical structures, the shape and dimensions of said fixture corresponding substantially to the shape and configuration of said channel or groove, said data having been generated by non-invasive measurements which correspond substantially to the dimensions of the affected part of the jawbone, and means on said fixture for receiving a prosthetic device.

2. The assembly of claim 1 wherein the implant is made of titanium.

3. The assembly of claim 2 wherein the fixture has a cross-section which is generally square, circular, rectangular, trapezoidal or triangular.

4. The assembly of claim 3 wherein the fixture spans a dimension greater than one tooth space when placed within the channel or groove.

5. The assembly of claim 4 wherein the means for receiving the prosthetic device are capable of receiving a healing plug for said fixture.

6. The assembly of claim 5 wherein the screw-receiving means are positioned in at least three locations on the fixture.

7. The assembly of claim 1 wherein the prosthetic device is capable of holding a plurality of teeth.

8. The method for producing a device implantable into the mandible or maxilla which comprises
 a) producing a jig adapted to be placed onto the mandible or maxilla, said jig having dimensions which essentially correspond to the dimensions of the affected part of the mandible or maxilla whereby a close fit of the interface between the jig and the bony surface of the mandible or maxilla is obtained, said jig being adjusted to accommodate means for producing a channel in the bone,
 b) producing in the bone a channel having dimensions sufficient to accomodate an implant which maximizes the utilization of cortical bone,
 c) providing in the channel of the bone an implant prepared from non-invasive measurements on the mandible,
 d) providing on the implant above the surface of the gum, a prosthetic device capable of holding a plurality of teeth.

* * * * *